United States Patent [19]
Toriyama et al.

[11] Patent Number: 4,772,573
[45] Date of Patent: Sep. 20, 1988

[54] HIGH-STRENGTH SINTERED ARTICLE OF CALCIUM PHOSPHATE COMPOUND, RAW MATERIAL FOR PRODUCTION OF SAID SINTERED ARTICLE, AND METHOD FOR PRODUCTION OF SAID SINTERED ARTICLE

[75] Inventors: Motohiro Toriyama, Nagoya; Sukezo Kawamura, Inuyama, both of Japan

[73] Assignees: Agency of Industrial Science and Technology; Ministry of International Trade and Industry, both of Tokyo, Japan

[21] Appl. No.: 69

[22] Filed: Jan. 2, 1987

[30] Foreign Application Priority Data

Jan. 10, 1986 [JP] Japan ................................ 61-3880
Jan. 17, 1986 [JP] Japan ................................ 61-8726

[51] Int. Cl.$^4$ ............................................. C04B 35/02
[52] U.S. Cl. ........................................ 501/1; 501/128; 106/35
[58] Field of Search ..................... 501/128, 1; 106/35

[56] References Cited

U.S. PATENT DOCUMENTS

| | | | |
|---|---|---|---|
| 4,308,064 | 12/1981 | Takami et al. | 501/1 |
| 4,376,168 | 3/1983 | Takami et al. | 501/1 |
| 4,503,157 | 3/1985 | Hatahira | 501/1 |
| 4,560,666 | 12/1985 | Yoshida et al. | 501/10 |
| 4,613,577 | 9/1986 | Tagai et al. | 501/35 |
| 4,643,982 | 2/1987 | Kasuga et al. | 501/10 |

*Primary Examiner*—William R. Dixon, Jr.
*Assistant Examiner*—Anthony Green
*Attorney, Agent, or Firm*—Oblon, Fisher, Spivak, McClelland & Maier

[57] ABSTRACT

Sintered article suitable for artificial bones, for example, containing a calcium phosphate compound as a main component and additionally containing spinel or magnesium oxide formed by sintering magnesium oxalate dihydrate. This sintered article is produced by adding alumina and silica or magnesium oxalate dihydrate to a calcium phosphate compound and firing the resultant mixture.

7 Claims, No Drawings

HIGH-STRENGTH SINTERED ARTICLE OF CALCIUM PHOSPHATE COMPOUND, RAW MATERIAL FOR PRODUCTION OF SAID SINTERED ARTICLE, AND METHOD FOR PRODUCTION OF SAID SINTERED ARTICLE

FIELD OF THE INVENTION AND RELATED ART STATEMENT

This invention relates to a sintered article having calcium phosphate compound as a main component, possessing high strength and toughness, and suitable as a prosthetic material for artificial bones, artificial root of tooth, and artificial joints, to a raw material for the production of the sintered article, and to a method for the production of the sintered article by the use of the raw material.

Calcium phosphate compounds such as hydroxy apatite and tricalcium phosphate are the main components of such bio-inorganic substances as bones and teeth and possess outstanding bioaffinity as shown by the fact that they lack toxicity to living bodies, and have ability to join with osseous tissues, ability to substitute for neoplastic bones, and ability to adhere to the epithelium. Thus, sintered articles of calcium phosphate compounds have been attracting growing attention as prosthetic materials, typically artificial bones, artificial roots of teeth, artificial joints, artificial tracheas, and artificial blood vessels. For the production of sintered articles of calcium phosphate compound as such prosthetic materials, a method must be established which fulfils the following three requirements: (1) The sintered articles produced thereby should possess high strength, (2) the sintered articles should be formed easily in complex shapes and (3) the method should be suitable for small lot production of a wide variety of articles.

The methods heretofore adopted for the production of sintered articles of calcium phosphate compound fall under the four types; (1) the metal die press method, (2) the rubber press method, (3) the hot press method, and (4) the hydrostatic pressure sintering method. The metal die press method and the rubber press method respectively use a metallic mold and a rubber mold which are to be filled to capacity with a powdered raw material. The raw material is pressure formed in one direction in the former mold and evenly in all directions in the latter mold. The shaped article consequently removed from either of the molds is fired.

In the hot press and hydrostatic methods, sintering can, if desired, be carried out under application of pressure, but this requires expensive equipment.

Even by these methods, it is not easy to obtain, on a commercial scale, sintered articles possessing sufficient strength and toughness fit for utility as artificial bones.

OBJECT AND SUMMARY OF THE INVENTION

An object of this invention is to offer a solution to the problem described above and, therefore, provide a high-strength sintered article containing calcium phosphate compound as a main component and suitable for convenient and economic commercialization, a raw material for the production of the sintered article, and a method for the production of the sintered article.

To be specific, this invention is directed to a sintered article suitable for artificial bones, for example, containing a calcium phosphate compound as a main component and additionally containing spinel or magnesium oxide formed by sintering magnesium oxalate, a raw material for sintering prepared by adding silica and alumina or magnesium oxalate dihydrate to calcium phosphate compound, a method for the production of the sintered article, which comprises forming the raw material in a powdered state or as a slip and thereafter firing the shaped raw material.

DETAILED DESCRIPTION OF THE PREFERRED EMBODIMENT

The term "calcium phosphate compound" as used in this specification substantially refers to at least one member selected from the group consisting of tricalcium phosphate and hydroxy apatite.

First, the raw material prepared by admixing calcium phosphate compound with silica and alumina will be described. The inventors have found that when tricalcium phosphate or hydroxy apatite powder is mixed with silica powder and alumina powder in a prescribed ratio, the resultant mixture is formed by any of the conventional forming methods such as press forming method and slip casting method, and the formed mixture is fired, there is obtained a calcium phosphate compound sintered article having needle crystals of mullite formed. In this case, the amount of the silica powder and that of the alumina powder to be added are in the range of 1 to 10 parts by weight and 2 to 10 parts by weight respectively, based on 100 parts by weight of the amount of the calcium phosphate compound. If their amounts are smaller than the lower limits, the amount of crystals to be formed is small and the sintered article acquires insufficient strength. If their amounts are larger than the upper limits, the sintered article fails to possess attributes necessary for artificial bones. When the raw material contains these powders within the range mentioned above, the produced sintered article contains 0.5 to 5% by weight of mullite crystals.

Now, the raw material prepared by admixing calcium phosphate compound with magnesium oxalate dihydrate will be described. This raw material can be directly molded and then fired. When this material is given adjusted slip and formed by the slip casting method and the shaped calcium phosphate compound article is dried and then sintered, there can be obtained a sintered article of calcium phosphate compound with extremely high strength.

Specifically, this invention provides a method for the production of a high-strength sintered article of calcium phosphate compound without reference to complexity of the shape, which method comprises mixing calcium phosphate compound powder (such as tricalcium phosphate or hydroxy apatite) with 0.2 to 5% by weight, based on the calcium phosphate compound powder, of magnesium oxalate dihydrate, preparing a slip by adding to the mixed powder of calcium phosphate compound 0.7 to 1.2 times the weight of the mixed powder of an aqueous solution of ammonium salt of acrylic acid-maleic acid copolymer (ammonium salt concentration in the acrylic acid-maleic acid copolymer 0.5 to 6%), casting the slip in a female die made of a highly workable water-absorbing material (such as, for example, gypsum or macromolecular porous substance), drying the shaped article of calcium phosphate obtained by the casting, and firing the dry shaped article at a temperature in the range of 1,050° to 1,400° C.

If the amount of the magnesium oxalate dihydrate powder is less than 0.2% by weight, the sintered article does not possess sufficient strength. If the amount exceeds 5% by weight, the sintered article acquires insufficient attributes for artificial bones, for example.

In the method of this invention, magnesium oxalate is oxidized into magnesium oxide during the process of sintering and the magnesium oxide serves to promote the sintering of calcium phosphate compound. The amount of magnesium oxide to be contained in the sintered article falls in the range of 0.05 to 1.36% by weight. Addition of magnesium oxide, magnesium acetate, magnesium lactate, or magnesium hydroxide results in a great increase of the viscosity of the slip of calcium phosphate compound and prevents desired preparation of the slip for the slip casting. The optimum sintering temperature for the formation of the sintered article can be controlled by the amount of magnesium oxalate to be added. Specifically, the optimum sintering temperature rises in proportion as the amount of magnesium oxalate to be added increases. The shaped article of calcium phosphate compound using tricalcium phosphate as a main component thereof is sintered at a temperature in the range of 1,050° to 1,200° C. and the shaped article of calcium phosphate compound using hydroxy apatite as a main component thereof at a temperature in the range of 1,150° to 1,400° C. The ammonium salt of the acrylic acid-maleic acid copolymer enhances the deflocculating property of the calcium phosphate compound powder during the preparation of the slip and then, after the shaped article is dried, enhances the strength of the dried shaped article. During the course of the firing, it is completely oxidized and is not allowed to survive in the sintered article of calcium phosphate compound. The concentration and amount of the aqueous solution of the ammonium salt of the acrylic acid-maleic acid copolymer can be changed in accordance with the size of the shaped article and the complexity of shape of the shaped article.

The method of this invention enables a sintered article to be formed easily without reference to complexity of shape and permits production of a sintered article of calcium phosphate compound of high strength. Thus, the production of a variety of sintered articles in small lots can be effected with an inexpensive and simple apparatus. The method proves to be an extremely economic approach to the production of sintered articles.

The sintered articles of calcium phosphate compound which are obtained by the method of this invention possesses high strength and toughness and, therefore, can be used advantageously as prosthetic materials such as, for example, artificial bones, artificial roots of teeth, artificial joints, artificial blood vessels, and artificial tracheas.

Now, the present invention will be described more specifically below with reference to working examples.

EXAMPLE 1

Tricalcium phosphate powder was mixed with 2.5% by weight of silica powder and 4% by weight of alumina powder, both based on the amount of the tricalcium phosphate powder. The resultant mixture was molded by the slip casting method. The shaped article was dried and then fired at 1,300° C. for one hour.

The product was a sintered article of tricalcium phosphate reinforced with needle crystals of mullite incorporated therein. The bending strength of this sintered article was 1,900 kgf/cm$^2$.

The mullite content of the sintered article was 2% by weight.

EXAMPLE 2

The procedure of Example 1 was faithfully repeated, except that the amount of alumina powder added was changed to 5% by weight and the sintering temperature was changed to 1,350° C.

The product was a sintered article of tricalcium phosphate reinforced with mullite contained therein. The bending strength of this sintered article was 1,800 kgf/cm$^2$. The mullite content thereof was 3% by weight.

EXAMPLE 3

The procedure of Example 1 was faithfully repeated, except that the tricalcium phosphate powder was changed to hydroxy apatite powder and the molding was carried out by the metal press molding method.

The product was a sintered article of hydroxy apatite reinforced with mullite contained therein. The bending strength of this sintered article was 2,000 kgf/cm$^2$. The mullite content of this sintered article was 2% by weight.

COMPARATIVE EXPERIMENT 1

Tricalcium phosphate powder was mixed with 4% by weight of alumina powder, based on the amount of the tricalcium phosphate powder. The resultant mixture was molded by the slip casting method. The shaped article was dried and then fired at a temperature in the range of 1,050° to 1,400° C.

The product was a sintered article possessing a mixed phase of tricalcium phosphate with alumina, no matter what temperature was used for the sintering in the aforementioned range. The bending strength of any of the sintered articles obtained was below 700 kgf/cm$^2$.

COMPARATIVE EXPERIMENT 2

The procedure of Example 3 was faithfully repeated, except that the use of the alumina powder in the raw material powder was omitted.

The product was a sintered article composed of a mixed phase of hydroxy apatite and silica. The bending strength of this sintered article was 950 kgf/cm$^2$.

EXAMPLE 4

A calcium phosphate slip was prepared by mixing 50 g of tricalcium phosphate powder with 300 mg of magnesium oxalate dihydrate and adding to the resultant mixed powder 45 ml of an aqueous solution of the ammonium salt of 4% acrylic acid-maleic acid copolymer. A shaped article of calcium phosphate was obtained by casting this calcium phosphate slip in a female die made of gypsum. This shaped article was dried and then fired at 1,150° C. The magnesium oxide content of this sintered article was 0.16% by weight. This product was a sintered article of calcium phosphate having a bending strength of 2,100 kgf/cm$^2$.

EXAMPLE 5

The procedure of Example 4 was faithfully repeated, except that the amount of the magnesium oxalate dihydrate was changed to 1.5 g and the sintering temperature was changed to 1,200° C. The product was a sintered article of calcium phosphate having a bending strength of 1,700 kgf/cm$^2$. The magnesium oxide content of this sintered article was 0.82% by weight.

COMPARATIVE EXPERIMENT 3

The procedure of Example 4 was faithfully repeated, except that the addition of the magnesium oxalate dihydrate was omitted. The product was a sintered article of calcium phosphate having a bending strength of 500 kgf/cm$^2$.

What is claimed is:

1. A sintered article consisting essentially of tricalcium phosphate and 0.5 to 5% weight of needle crystals of mullite prepared by firing at a temperature of 1,100° to 1,500° C. a composition consisting essentially of tricalcium phosphate, silica in amount of 1 to 10% by weight, and alumina in an amount of 2 to 10% by weight, both based on the amount of tricalcium phosphate.

2. The sintered article of claim 1, wherein the silica and alumina are in the form of a powder.

3. A raw material for the preparation of the sintered article of claim 1, consisting essentially of a mixture of tricalcium phosphate, silica in an amount of 1 to 10% by weight and alumina in an amount of 2 to 10% by weight, both based on the amount of tricalcium phosphate.

4. The raw material of claim 3, wherein the silica and alumina are in the form of a powder.

5. The raw material of claim 3 in the form of a slip.

6. A method for the preparation of the sintered article of claim 1, comprising firing at a temperature of 1,100° to 1,500° C. a composition consisting essentially of tricalcium phosphate, silica in an amount of 1 to 10% by weight, and alumina in an amount of 2 to 10% by weight, both based on the amount tricalcium phosphate.

7. The method of claim 6, wherein the silica and alumina are in the form of a powder.

* * * * *